United States Patent [19]

Mori

[11] Patent Number: 4,794,925
[45] Date of Patent: Jan. 3, 1989

[54] SOLAR RAY ENERGY RADIATING DEVICE FOR USE IN MEDICAL TREATMENT

[76] Inventor: Kei Mori, 3-16-3-501, Kaminoge, Setagaya-ku, Tokyo, Japan

[21] Appl. No.: 70,484

[22] Filed: Jul. 7, 1987

[30] Foreign Application Priority Data

Jul. 10, 1986 [JP] Japan .................................. 61-162376

[51] Int. Cl.⁴ .......................... A61N 3/00; F21V 9/00; G02F 1/13
[52] U.S. Cl. .................................... 128/397; 362/293; 350/331 R
[58] Field of Search ............................ 362/32, 34, 293; 350/362, 349, 331 R, 332; 128/395–398

[56] References Cited

U.S. PATENT DOCUMENTS

| | | | |
|---|---|---|---|
| 3,499,112 | 3/1970 | Heilmeier et al. | 350/331 R |
| 3,575,491 | 4/1971 | Heilmeier | 350/332 |
| 3,882,490 | 5/1975 | Tashiro et al. | 350/331 R |
| 4,030,109 | 6/1977 | Hecker | 350/331 R |
| 4,364,639 | 12/1982 | Sinclair et al. | 350/331 R |
| 4,406,513 | 9/1983 | Raphael | 350/331 R |
| 4,456,335 | 6/1984 | Mumford | 350/331 R |
| 4,475,031 | 10/1984 | Mockovciak | 350/331 R |

*Primary Examiner*—Richard C. Pinkham
*Assistant Examiner*—Mark S. Graham
*Attorney, Agent, or Firm*—Jordan and Hamburg

[57] ABSTRACT

A solar ray energy radiating device for use in medical treatment. The device comprises an upper plate having a hole through which the light-emitting end of an optical conductor cable is inserted at the approximate central portion of the upper plate, a diffused reflecting type liquid-crystal plate being disposed so as to oppose the light-emitting end of the optical conductor cable, and a frame body for unitarily mounting thereon the upper plate and the diffused reflecting type liquid-crystal plate. The light ray energy passing through the liquid-crystal plate is controlled by changing the voltage applied thereto.

4 Claims, 1 Drawing Sheet

SOLAR RAY ENERGY RADIATING DEVICE FOR USE IN MEDICAL TREATMENT

BACKGROUND OF THE INVENTION

The present invention relates to a solar ray energy radiating device for medical treatment, in particular, a light ray radiating device for use in medical treatment which radiates light ray energy corresponding to the visible light ray components of solar rays onto a diseased part or a desired portion of a patient in order to administer various kinds of medical treatments, or which radiates the same onto the surface of a person's skin for administering beauty treatments or for promoting health.

In recent years, a large number of persons suffer from incurable diseases such as arthritis, neuralgia and rheumatism, or pain from injury scars or a bone fracture scars, or pain from ill-defined diseases. Furthermore, persons cannot avoid having their skin grow old which progresses gradually from a comparatively young age. On the other hand, the present applicant has previously proposed to focus solar rays or artificial light rays by use of lenses or the like, to guide thee same into an optical conductor, and to transmit those solar rays or artificial light rays onto an optical desired place through the optical conductor. Those light rays transmitted in such a way are employed for use in illuminating or for other like purposes, for example, to cultivate plants, chlorella, and the like. In the process, visible light rays not containing ultraviolet rays, infrared rays, etc. promote a living body reaction and the same appears to promote the health of a person or prevent the person's skin from growing old. Furthermore, those visible light rays appear to have noticeable beneficial effects for recovering from arthritis, neuralgia, bedsores, rheumatism, injury scars, bone fracture scars, or the like, and for relieving pain from those diseases. Such beneficial effects have been witnessed by the present applicant.

SUMMARY OF THE INVENTION

It is an object of the present invention to provide a solar ray energy radiating device for use in medical treatment.

It is another object of the present invention to provide a light ray radiating device for medical treatment which is also capable of administering beauty treatments or for promoting general health by effectively radiating light rays corresponding to the visible light ray components of the sun's rays.

It is another object of the present invention to provide a light ray radiating device which radiate a visible light rays containing no harmful components such as ultraviolet rays or infrared rays, etc.

It is another object of the present invention to provide a light ray radiatiäng device in which the light ray energy to bee radiated onto a diseased part of a patient can be easily intercepted, and the intensity thereof can be adjusted.

It is another object of the present invention to provide a light ray radiating device in which the light rays emitted from the optical conductor cable can be adequately diffused in order to employ them as ordinary light rays for illumination, when radiation as a medical treatment is not required.

DESCRIPTION OF THE PREFERRED EMBODIMENTS

Figure 1:
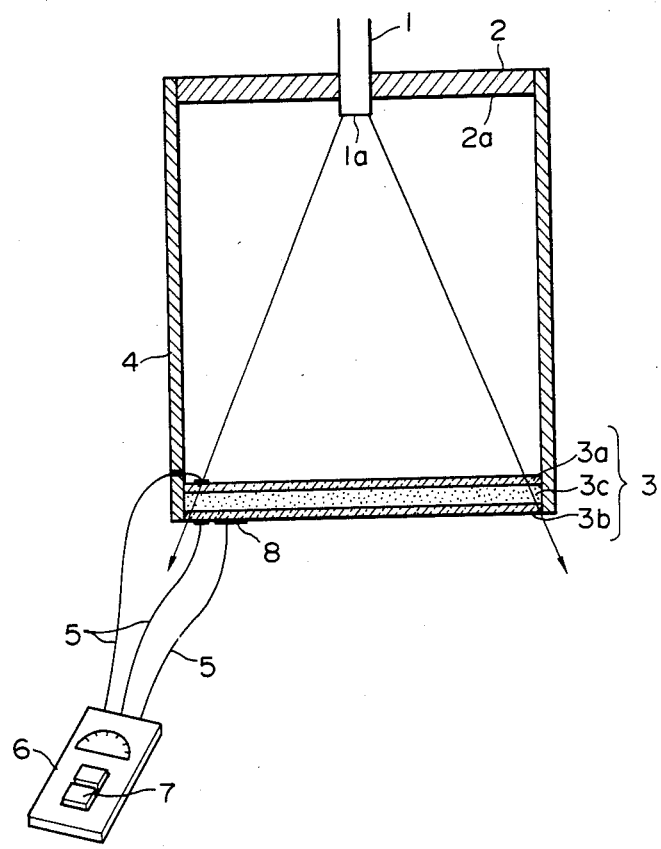
FIG. 1 is a construction view for explaining an embodiment of a solar ray energy radiating device for use in medical treatment according to the present invention.

FIG. 1 is a construction view for explaining an embodiment of a light ray radiation device for use in medical treatment according to the present invention. In FIG. 1, 1 is an optical conductor cable. Solar rays are guided into the optical conductor cable 1 from an end portion thereof not shown and transmitted therethrough. The light rays ( the white-colored light rays) corresponding to the visible light ray components of solar rays are transmitted through an optical conductor cable 1 in such a manner as was previously proposed in various ways by the present applicant. In the same FIG., 2 is an upper plate having a hole through which a light-emitting end 1a of an optical conductor cable 1 is inserted at the approximate central portion of the upper plate, 3 a diffused reflecting type liquid-crystal plate disposed so as to oppose the light-emitting end 1a of the optical conductor cable 1, and 4 a frame member for unitarily mounting thereon the upper plate 2 and the diffused reflecting type liquid-crystal plate 3.

The liquid-crystal plate 3 comprises of transparent electrode plates 3a and 3b and a diffused reflecting liquid crystal 3c hermetically sealed between those electrode plates 3a and 3b. The reflection rate of the diffused reflecting liquid crystal 3c changes in accordance with the voltage applied acros the electrodes 3a and 3b. For instance, the liquid crystal becomes transparent at 0V, and the same is diffused and reflected at 10V.

In FIG. 1, 5 represents lead wires for applying the voltage across the electrodes 3a and 3b and 6 a power supply device. To state it in the simplest way, the diffused reflecting type liquid-crystal plate 3 can be employed as either a diffused reflecting plate or a transparent plate by turning on or turning off the switch 7 mounted on the power supply device 6. The light-emitting end portion 1a of the optical conductor cable 1 is disposed at the approximate central portion of the upper plate 2, and the solar ray energy transmitted through the optical conductor cable 1 is radiated toward the diffused reflecting type liquid-crystal plate 3.

At the time of administering medical treatment, the outside of the liquid crystal 3 is directed to a portion of the person to be treated or opposed to the same at a desired distance apart therefrom. And further, the switch 7 is turned off and the light rays consisting of the visible light ray components transmitted through the optical conductor cable 1, as mentioned before, are radiated through the diffused reflecting type liquid-crystal plate 3 onto the diseased part or the desired portion of the patient or onto another place which needs radiation.

As mentioned above, the light rays to be radiated onto the diseased part of a patient are the light rays corresponding to the visible light ray components of the solar rays which contain therein neither ultraviolet nor infrared rays. Thereby, medical treatment can be performed without causing any harmful effects. However, it is preferable that the radiation of a diseased part be capable of being switched on or switched off at any desirable time duing a medical treatment. For instance, if the light to be radiated is diffused and reflected, those light rays are of small brightness and are suitable for ordinary illumination. According to the present invention, the light rays to be radiated are converted to soft ordinary light rays or to light rays suitable for medical treatment in order to focus the same onto a diseased part by turning on and off the afore-mentioned switch 7 as needed. The on-off control of the diffused reflecting liquid-crystal plate 3 by use of a switch 7 has been described heretofore. However, it might be possible to obtain a desired intensity of light rays by changing the voltage applied across the electrode plates 3a and 3b continuously by the use of a variable resistor or the like or by changing stepwise the same by using a step switch or the like, or might also be possible to employ as ordinary light rays. Furthermore, a light sensor 8 is installed at the outside of the diffused reflecting type liquid-crystal plate 3b, and the output voltage of the light sensor 8 is displayed on the panel of the power supply device 6. On that occasion, it may be also possible to change the voltage applied to the diffused reflecting type liquid-crystal plate 3 observing this displayed value and thereby obtaining the most suitable intensity of radiation.

And further, in the above-mentioned embodiment, the inner surface 2a of the upper plate 2 is formed as a reflecting surface and the frame body 4 is made of a transparent body, a semi-transparent body, or a reflecting body. In such a construction, the light rays emitted from the optical conductor cable 1 can be varied and radiated onto a desired place.

As is apparent from the foregoing description, according to the present invention, the light ray energy to be radiated onto a diseased part of a patient can be easily intercepted, and the intensity thereof can be adjusted. In particular, when radiation as a medical treatment is not required, the light rays emitted from the optical conductor cable can be adequately diffused in order to employ them as ordinary light rays for illumination. In such a way, it may be possible to obtain a light source of low intensity without glare.

I claim:

1. A solar ray energy radiating device for use in medical treatment, said device comprising an upper plate having a hole through which the light-emitting end of an optical conductor cable is inserted at the approximate central portion of said upper plate, said optical conductor cable carrying light ray energy, a diffused reflecting type liquid-crystal plate being disposed so as to oppose said light-emitting end of said optical conductor cable, a frame body for unitarily mounting thereon said upper plate and said diffused reflecting type liquid-crystal plate, a light sensor for detecting the light ray energy radiated from said optical conductor cable, said light sensor being installed at the outside of said diffused reflecting type liquid-crystal plate, and a variable voltage source connected to said liquid-crystal plate for controlling the diffusivity of said liquid-crystal plate thereby controlling the amount of the light ray energy passing through said liquid-crystal plate, the voltage applied by said variable voltage source to said liquid-crystal plate being changed in accordance with the output signal generated by said light sensor.

2. A solar ray energy radiating device for use in medical treatment, said device comprising an upper plate having a hole through which the light-emitting end of an optical conductor cable is inserted at the approximate central portion of said upper plate, said upper plate having an inside surface which acts as a mirror, said optical conductor cable carrying light ray energy, a diffused reflecting type liquid-crystal plate being disposed so as to oppose said light-emitting end of said optical conductor cable, a frame body for unitarily mounting thereon said upper plate and said diffused reflecting type liquid-crystal plate, and a variable voltage source connected to said liquid-crystal plate for controlling the diffusivity of said liquid-crystal plate thereby controlling the amount of the light ray energy passing through said liquid-crystal plate.

3. A solar ray energy radiating device for use in medical treatment, said device comprising an upper plate having a hole through which the light-emitting end of an optical conductor cable is inserted at the approximate central portion of said upper plate, said optical conductor cable carrying light ray energy, a diffused reflecting type liquid-crystal plate being disposed so as to oppose said light-emitting end of said optical conductor cable, a transparent frame body for unitarily mounting thereon said upper plate and said diffused reflecting type liquid-crystal plate, and a variable voltage source connected to said liquid-crystal plate for controlling the diffusivity of said liquid-crystal plate thereby controlling the amount of the light ray energy passing through said liquid-crystal plate.

4. A solar ray energy radiating device for use in medical treatment, said device comprising an upper plate having a hole through which the light-emitting end of an optical conductor cable is inserted at the approximate central portion of said upper plate, said optical conductor cable carrying light ray energy, a diffused reflecting type liquid-crystal plate being disposed so as to oppose said light-emitting end of said optical conductor cable, a semi-transparent frame body for unitarily mounting thereon said upper plate and said diffused reflecting type liquid-crystal plate, and a variable voltage source connected to said liquid-crystal plate for controlling the diffusivity of said liquid-crystal plate thereby controlling the amount of the light ray energy passing through said liquid-crystal plate.

* * * * *